(12) United States Patent
Orme

(10) Patent No.: US 8,383,405 B2
(45) Date of Patent: Feb. 26, 2013

(54) METHODS OF USING IDEOTYPICALLY MODULATED PHARMACOEFFECTORS FOR SELECTIVE CELL TREATMENT

(75) Inventor: Jacob Orme, Coppell, TX (US)

(73) Assignee: Imperium Biotechnologies, Inc., Coppell, TX (US)

( * ) Notice: Subject to any disclaimer, the term of this patent is extended or adjusted under 35 U.S.C. 154(b) by 173 days.

(21) Appl. No.: 12/790,931

(22) Filed: May 31, 2010

(65) Prior Publication Data

US 2011/0294188 A1 Dec. 1, 2011

(51) Int. Cl.
*C12N 5/00* (2006.01)
*C12N 5/02* (2006.01)
*C12Q 1/68* (2006.01)
*A61K 48/00* (2006.01)

(52) U.S. Cl. .................. 435/375; 435/6.1; 514/44 R

(58) Field of Classification Search .................. None
See application file for complete search history.

(56) References Cited

U.S. PATENT DOCUMENTS

| 4,724,232 A | 2/1988 | Rideout |
| 4,861,707 A | 8/1989 | Ivanoff |
| 4,867,973 A | 9/1989 | Goers |
| 5,846,565 A | 12/1998 | Brem |
| 2004/0009167 A1 | 1/2004 | Rider |
| 2005/0267061 A1 | 12/2005 | Martin |
| 2010/0323001 A1 * | 12/2010 | Pachuk .................. 424/450 |

OTHER PUBLICATIONS

Chao Y et al. PLoS Biology, 3(6):1079-1087, Jun. 2005.*
Notification of Transmittal of the International Search Report and the Written Opinion of the International Searching Authority, or the Declaration dated Jan. 9, 2012 in connection with International Patent Application No. PCT/US11/38393.

* cited by examiner

*Primary Examiner* — Robert Landsman

(57) ABSTRACT

In a method embodiment, a method includes introducing a plurality of Ideotypically Modulated Pharmacoeffectors (IMP) into a population of cells. Each IMP may include a detection domain and an activation domain. One or more epitopes is bound by the detection domain. The activation domain is activated in response to the binding. Applications may include but are not limited to viral infections, other intracellular infections, cancers, vector-borne diseases, autoimmune diseases, cellular diseases, cellular enhancement, and research.

14 Claims, 2 Drawing Sheets

METHODS OF USING IDEOTYPICALLY MODULATED PHARMACOEFFECTORS FOR SELECTIVE CELL TREATMENT

TECHNICAL FIELD OF THE INVENTION

This invention is related generally to ideotype-specific treatments of cells and organisms, and more particularly to ideotype-specific treatments of cells and organisms using engineered Ideotypically Modulated Pharmacoeffectors (IMPs).

BACKGROUND

In the human body, each cell type expresses a unique assortment of proteins, lipids, sugars, nucleotide sequences, and other metabolites. Each of these is a potential antigen, having epitopes with which a molecule having predetermined affinity can interact. The expression of said antigens is modified by the status of the cell and by its environment. This expression becomes further modified when viruses or intracellular bacteria introduce foreign materials into the cell as they infect. Viruses in particular hijack the cell machinery and produce many virion copies that bud off from the cell and infect other cells.

When a person becomes infected by a virus, the immune system has various mechanisms that attempt to detect and destroy infected cells. Unfortunately, many viruses have adapted mechanisms to evade this protection and send duplicated virions to infect other cells. These adaptations succeed because the viruses have two important features: speedy replication and rapid mutation rates.

SUMMARY

In a method embodiment, a method includes introducing a plurality of engineered Ideotypically Modulated Pharmacoeffectors (IMPs) into a population of cells. Each IMP may include a detection domain and an activation domain. One or more epitopes is bound by the detection domain. The activation domain is activated in response to the binding.

Certain embodiments of the method may have a number of technical advantages. For example, some embodiments may be capable of terminating diseased or disease-causing cells. Some other embodiments may include enhancing cells. Some further embodiments may be capable of eliminating carriers of zoonotic diseases. Still embodiments may reduce complications associated with transplants. Various embodiments may include some, all, or none of the above advantages. Particular embodiments may include other advantages.

BRIEF DESCRIPTION OF THE DRAWINGS

In the drawings, numbered objects are consistent across figures.

DESCRIPTION OF EXAMPLE EMBODIMENTS

Figure 1:
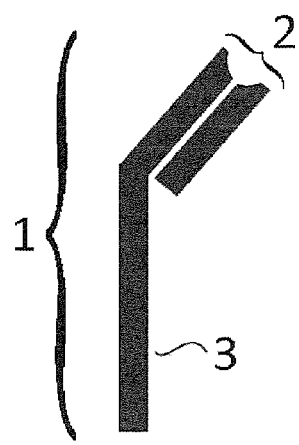
FIG. 1 shows one example of an engineered Ideotypically Modulated Pharmacoeffector including a detection domain and an activation domain according to one embodiment.

FIG. 1 shows one example of an engineered Ideotypically Modulated Pharmacoeffector (1) according to one embodiment. In the illustrated example, an IMP (1) includes a detection domain (2) and an activation domain (3). The term "detection domain" as used herein refers to any molecule (e.g. protein, nucleotide sequence, lipid) that has affinity for a molecule of interest. The term "activation domain" as used herein refers to any molecule (e.g. protein, nucleotide sequence, substance) that may be activated to interact with the cell or its environment in response to the binding of the detection domain. In certain embodiments, "engineered" Ideotypically Modulated Pharmacoeffectors or IMPs (1) may refer to a nonnaturally occurring manufacture or composition of biological matter having a distinctive use, as described further below.

Figure 2A:
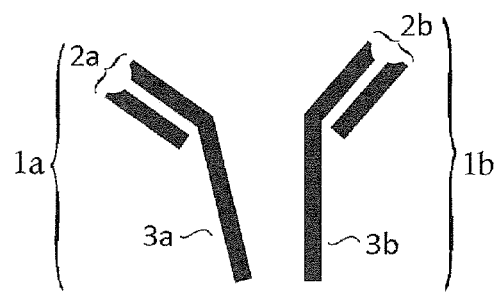
FIG. 2A shows one example of multiple unbound Ideotypically Modulated Pharmacoeffectors that may be introduced into a population of cells according to one embodiment.
Figure 2B:
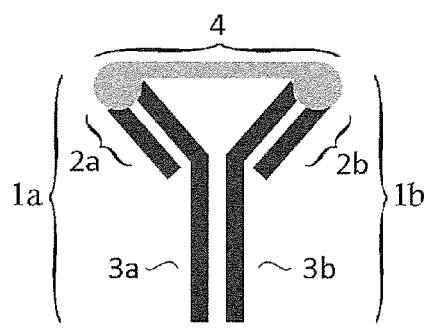
FIG. 2B shows one example of binding of multiple adjacent ideotypical epitopes to the detection domains of multiple Ideotypically Modulated Pharmacoeffectors according to one embodiment.

FIG. 2A shows one example of multiple unbound Ideotypically Modulated Pharmacoeffectors (1a, 1b) that may be introduced into a population of cells according to one embodiment. The detection domains (2a, 2b) of these IMPS (1a,1b) have affinity for adjacent epitopes on a predetermined target antigen (4) when present in the cell of a particular ideotype. The term "epitope" as used herein refers to any part of a molecule of interest to which a detection domain, as defined above, binds. The terms "ideotype," "ideotypical," and "ideotypically" as used herein refer to the uniqueness of the set of antigens (and their concomitant epitopes) expressed in or on a subset of cells. The detection domains (2a,2b) may be identical or different, depending on the application. For instance, in detecting antigens (4) with repetitive epitopes, identical detection domains (2a,2b) may be advantageous. The binding of more than one Ideotypically Modulated Pharmacoeffector (1a,1b) to adjacent epitopes results in the dimerization or multimerization of the activation domains (3a,3b). The terms "dimerization" and multimerization" as used herein refer to the colocalization of molecules, whether homologous or heterologous, changing the activity of said molecules. As with the detection domains, activation domains may be identical or different, depending on the application. For instance, an activation domain (3a,3b) for inducing cell death may be inactive Caspase-9 monomer, which—when dimerized—converts itself to an active form. In this case, an identical activation domain may be advantageous.

Figure 2C:
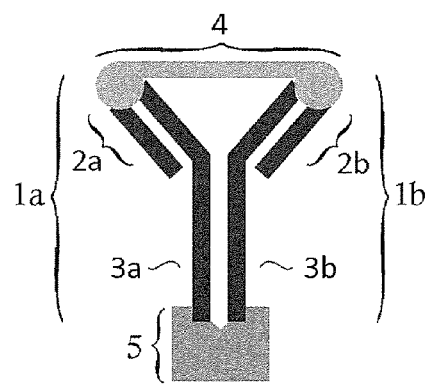
FIG. 2C shows the interaction of multimerized Ideotypically Modulated Pharmacoeffectors with endogenous cascade mediators according to one embodiment.

FIG. 2C shows the interaction of multimerized Ideotypically Modulated Pharmacoeffectors with endogenous cascade mediators (5) from a cell according to one embodiment. This induces a cascade of desired downstream effects in cells which contain the epitopes of the antigen of interest (4). The term "downstream effects" as used herein may refer to any biological result of the interaction of activation domains (3a, 3b) with endogenous molecules (5). In certain circumstances, the epitopes of the antigen of interest (4) may be expressed in a desired target cell type (i.e. ideotype), whether viral, cancerous, or otherwise of interest. As a result, these downstream effects may be induced in these target cells, conferring specificity of downstream effects. In some embodiments, a linker of some sort (e.g. collagen) may conjugate the detection and activation domains as pictured in FIG. 5. The length of this linker may be adjusted to maximize downstream effect.

There are a number of methods by which Ideotypically Modulated Pharmacoeffectors (1) may be manufactured. In one instance, a $F_{Ab}$ antibody fragment with specific affinity for the target epitopes may be covalently conjugated to an effector domain by a collagen linker by synthetic conjugating processes. In other instances, an aminophosphonate group may chemically connect the C terminus of a $F_{Ab}$ fragment with the N terminus of an inactive Caspase. In another instance, the genetic code for the entire complex may be introduced in a bacterial species that may mass-produce the complex as a unit or as subunits to be conjugated later. In still another instance, an anti-sense nucleotide sequence specific for target epitopes of nucleotide sequences in the cell could be chemically conjugated to an activation domain. This may be accomplished through carbodiimides. These instances are only some of the ways in which the embodiment could be manufactured and should not be considered limiting. Further examples of manufacturing of IMPS are described below with reference to FIGS. 2A-6.

Figure 3A:
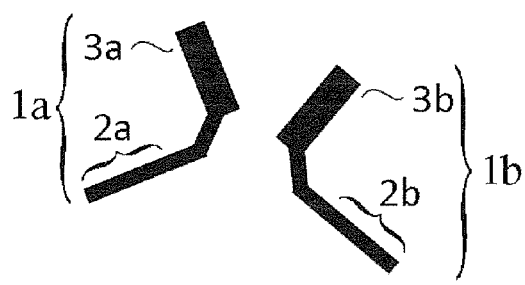
FIG. 3A shows one example of multiple unbound Ideotypically Modulated Pharmacoeffectors that may be introduced into a population of cells according to one embodiment.

FIG. 3A shows one example of multiple unbound Ideotypically Modulated Pharmacoeffectors (1a,1b) that may be introduced into a population of cells according to one embodiment. In this embodiment, detection domains (2a,2b) may comprise antisense nucleotide strands. In some embodiments, activation domains (3a,3b) may perform substantially the same functions as the activation domain shown in FIGS. 1-2C. These elements may be conjugated (1a,2a and 1b,2b) to form an IMP (1a,1b) by carbodiimides or by some other functional group or linker in a chemical process.

Figure 3B:
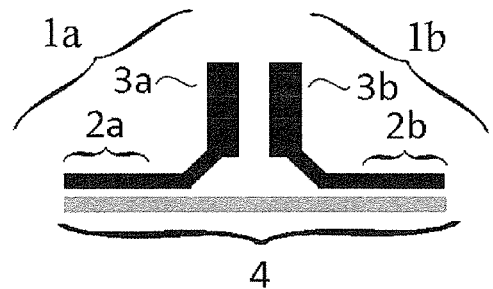
FIG. 3B shows one example of binding of multiple adjacent ideotypical epitopes to the detection domains of multiple Ideotypically Modulated Pharmacoeffectors according to one embodiment.

FIG. 3B shows one example of binding of multiple adjacent ideotypical epitopes (4) to the detection domains (2a,2b) of multiple Ideotypically Modulated Pharmacoeffectors according to one embodiment. In this embodiment, epitopes (4) may comprise nucleotide strands that may be unique to target cells of interest. In one embodiment, for instance, these strands may comprise a nucleotide sequence introduced by a virus as it infects a cell. In such a case, the detection domains (2a,2b) may be antisense nucleotide sequences that are complementary to that introduced by the virus.

Figure 3C:
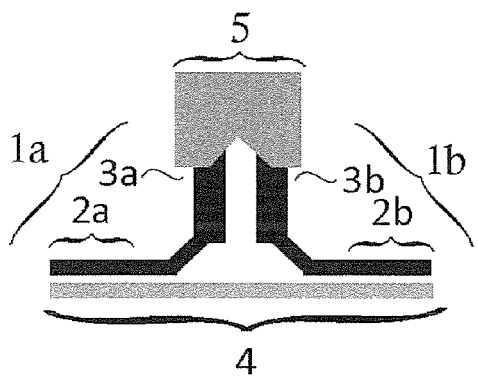
FIG. 3C shows the interaction of multimerized Ideotypically Modulated Pharmacoeffectors with endogenous cascade mediators according to one embodiment.

FIG. 3C shows the interaction of multimerized Ideotypically Modulated Pharmacoeffectors (1a,1b) with endogenous cascade mediators (5) according to one embodiment. In certain circumstances, the nucleotide epitope (4) may be expressed in a particular target cell type (i.e. ideotype), whether viral, cancerous, or otherwise of interest.

Figure 4:
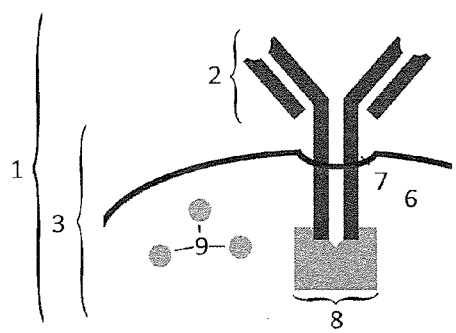
FIG. 4 shows an antibody or antibody-like complex capable of blocking the pore of a polymer pouch containing a number of effector molecules according to one embodiment.

FIG. 4 shows an antibody or antibody-like complex capable of blocking the pore (7) of a polymer pouch (6) containing a number of effector molecules (9) according to one embodiment. In certain embodiments, these antibodies or antibody-like complexes are held in the pores (7) by Fc-associated holder molecules (8). In some embodiments, this holder molecule may be Surface Protein A of *Staphylococcus aureus*. This blockage of the pore (7) may keep the effector molecules (8) from interacting with the cellular environment. The detection domain (2) of an embodiment may be specific for an epitope of interest, as those mentioned in previous embodiments. Binding of an epitope of interest induces conformational changes in the remainder of the complex, the activation domain (3). This dissociates the holder molecule (8), which in turn leaves the pore (7) free for effector molecules (9). The effector molecules (9) escape into the environment and interact, causing downstream effects. As in the previous embodiment, this could result in the death of the cell or some other downstream effect.

The introduction of IMPs into a cell for the detection of intracellularly-expressed epitopes as may be required in some embodiments may be accomplished by a number of mechanisms. Modified viral vectors (with the embodiment in the place of nucleotide material) may offer cell-specific or generalized introduction of the embodiments into the cell. Such constructs have been developed for gene therapy and may be modified for this purpose. Rather than injecting nucleotide material to be inserted into the host genome, these constructs may contain IMPs. Other potential methods include receptor-mediated endocytosis, which is also used by cells and viruses alike to take in exogenous materials. In one instance, an IMP may have a subunit with affinity for a surface receptor on all or a subset of cells. As a result of binding, the IMP may be brought into the cell. In some instances, an embodiment may be encapsulated in a colloid suspension, which may make the embodiment sufficiently amphiphilic to allow association with the lipid bilayer. Similarly, liposomes containing an IMP or IMPs may be coated with materials that may make them more likely to be taken up by a cell. For instance, an array of positive charges on a liposome containing an embodiment may allow non-specific cell bilayer association and fusion. The association of particular peptides may also help to encourage uptake of liposome contents. Different cellular compartments may require different delivery methods. These methods are only some of the ways in which the embodiment could be introduced into the cell and should not be considered limiting. Further, not all embodiments may need to be taken up into a cell to be effective. Further examples of cell entry mechanisms are described below with reference to FIGS. 2A-6.

A. Embodiments as May be Used in Viral Diseases

In various embodiments, viral diseases including but not limited to HIV may be treated. For instance, the use of the embodiment shown in FIGS. 1 and 2 may cause HIV-infected cells to die by apoptosis. The term "apoptosis" as used herein refers to programmed cell death in which the cell is induced by internal and/or external signaling to die. The term "apoptose" as used herein refers to the action of apoptosis of a cell. In one embodiment, the detection domain (2) of the Ideotypically Modulated Pharmacoeffectors (1) could be antibody fragments with specificity for adjacent epitopes (4) on HIV Reverse Transcriptase (HIV RT). HIV RT expresses epitopes that are unique and may not be found in normal, uninfected human cells. This may allow the differentiation of two ideotypes of cells: infected and uninfected. As previously described, the term "ideotype" as used herein refers to the uniqueness of the set of antigens expressed in or on a subset of cells. HIV RT is necessary for the virus to mount a successful cell invasion and will therefore be found in every HIV-infected cell. The activation domain (3) of an embodiment may be Fas-associated protein with death domain (FADD). When FADD trimerizes naturally in a cell in sufficient numbers, it causes the assembly of the death inducing signaling complexes (DISCs) that signal downstream to terminate the cell. Thus when three IMPs (1) bind adjacent epitopes (4) on HIV RT, the three FADD activation domains (3) may trimerize to cause downstream DISC formation. This may cause apoptosis of those cells in which sufficient DISCs are formed, which may be cells of the infected ideotype.

Another similar embodiment may be used in viral diseases. Detection domains (2a,2b) may comprise antisense nucleotide strands of RNA or DNA as shown in FIGS. 3A-C. In HIV infections, for instance, there are well-conserved RNA sequences that are introduced into the cell or produced by the cell as a result of the infection. A detection domain (2a,2b) of an embodiment may comprise antisense nucleotide strands that are complementary to adjacent conserved sequences of ideotypical viral nucleotides (4). These strands could be manufactured by using PCR or by transfecting bacteria to produce them. The activation domain (3a,3b) of an embodiment may be an inactive monomer of Caspase-9. When Caspase-9 dimerizes in nature, it becomes self-activating and causes cell apoptosis. A detection domain (2) and an activation domain (3a,3b) may be conjugated together through a phosphate group by the amine on the N terminus of the activation domain. In this artificial embodiment, the binding of the anti-sense strands (2a,2b) to adjacent portions of an HIV-specific nucleotide strand (4) may bring the activation domains (3a,3b) into contact such that they may dimerize. The cell may apoptose when this occurs in sufficient numbers.

While existing treatments may also be used to combat viral diseases including HIV, Ideotypically Modulated Pharmacoeffectors (IMPs) offer a number of advantages over these treatments. First and foremost, various embodiments of the present disclosure may allow the termination of infected cells before escape variants can be produced by the virus. Since the epitopes detected by IMPs may be selected such that they are conserved, even widely-mutated strains of any given virus may still express them. Further, all of the viral strains in a given cell—even those which have mutations that might make them superior escape variants—may be destroyed when a cell apoptoses. This means that IMPs, unlike existing treatments, may not naturally select evolutionarily superior strains of a virus. This may further mean that IMPS may not cause nor be affected by resistance mechanisms developed by the virus. This is in direct contrast to presently-available antivirals and antibiotics. Another advantage of IMPs may be their scope of effectiveness. While most current antiviral medications only interfere with the growth of the virus, IMPs may clear an infection completely. This gives the further advantage that IMPS may be much more cost-effective than existing treatments, since IMPs may not necessitate long-term treatment. In addition, the complete clearance of disease may eliminate the risk for further transmission. Related to all of the above-mentioned advantages, IMPs may avoid the unpleasant side effects of other treatments. These can include lipodystrophy, liver toxicity, and inflammation, amongst others. These side-effects lead a large fraction of patients to forego treatment (e.g. 25% of patients undergoing HAART for HIV infections). Without these side-effects, IMPs may result in higher treatment compliance.

While the above examples describe IMPs that would target HIV epitopes, these and other embodiments may be adjusted for other viral diseases. This could include, for example, viruses that cause the common cold, Dengue fever, Epstein-Barr, HPV, Hantavirus, various forms of hepatitis, herpes, influenza, rotavirus, and others. Thus the present embodiment should not be limited to these examples. Nor are these the only embodiments of IMPS by which HIV may be combated.

Various embodiments may also be used simultaneously (i.e. various detection domains and a variety of activation domains). This may give an advantage in that it may provide redundancy against potential resistance mechanisms.

B. Embodiments as May be Used in Other Infectious Intracellular Disease

Various embodiments of IMPS could also work against intracellular disease-causing organisms like bacteria or parasites. These disease-causing pathogens, including Rickettsiae and Chlamydia, can pose problems similar to those of viruses. They also express unique epitopes that may not be found in normal, uninfected cells. As previously, cells can be categorized into ideotypes of infected and uninfected.

In a particular embodiment to treat a Chlamydia infection, there may be a detection domain (2) that is a lectin. Lectins are found in nature and are capable of binding specific sugars, as are frequently expressed on the surface of specific bacteria. Some lectins, for instance, are quite specific to the sugars expressed on species of Chlamydia. The activation domain (3) in this embodiment may include various antimicrobials. In one embodiment using the pouch-based embodiment shown in FIG. 4, the effector molecules (9) may include antimicrobials like peptidoglycan lyase. Peptidoglycan lyase is an enzyme that digests the protective barrier found on the surface of most bacteria. On binding of lectins (2) to the specific sugars found on an invading bacterial cell wall in ideotypical cells, peptidoglycan lyase would be freed to digest bacterial cell barriers.

While the above example describes an IMP using one embodiment against a Chlamydia infection, many different embodiments are possible for various intracellular pathogens. For instance, the activation domain could signal apoptosis in the cell and the death of the cell could also eliminate the intracellular pathogen.

C. Embodiments as May be Used in Treating Cancers

Various embodiments of IMPS could also be used to treat and/or prevent cancers. Malignant cells may be ideotypical in that they may express epitopes that are either unique or enriched to these cells. The term "malignant cell" or "cancerous cell" as used herein refers to any cell that proliferates out of control as a result of genetic and/or metabolic changes in the cell. These epitopes may vary in their expression levels and distribution depending on the situation. Some epitopes are expressed in all or most cancer types, while others are only present in few. Some epitopes may never be expressed in non-malignant cells, while others may only have elevated expression levels in malignant cells.

In a particular embodiment to eliminate cancerous cells, there may be a detection domain (2) that is an antibody fragment specific for a mutated form of the protein p53 (4) found in some cancers. An activation domain (3) may comprise inactive Caspase-9 monomer. In cells of the malignant ideotype, the detection domains (2) of multiple IMPS (1) may bind the mutated p53 (4). Their activation domains (3) may dimerize to cause downstream signaling in the cell. When this signaling reaches sufficient levels, the cell may apoptose.

In another embodiment to eliminate prostate cancer, a detection domain (2) may comprise an antibody fragment specific for PSA (prostate specific antigen). While PSA is ideotypical of all prostate cells rather than just cancerous cells, it may be more effective in coping with prostate cancer after it has been diagnosed. An activation domain (3) may comprise inactive Caspase-9 monomer. If administered in smaller amounts, the embodiment may lower the threshold of natural cellular self-killing. In cancerous cells, this may induce cell death at a lower level than in non-diseased cells.

In still another embodiment to eliminate Chronic Myelogenous Leukemia (CML), cancerous immature leukocytes proliferate out of control as a result of a translocation. This translocation creates a fusion protein of the breakpoint cluster region and the Abl1 protein, resulting in unregulated growth. Detection domains (2a,2b) similar to the embodiment in FIG. 1 may be antibody $F_{Ab}$ fragments against part of the Abl1 protein and part of the breakpoint cluster region protein (4). Activation domains (3a,3b) may comprise inactive Caspase-9 monomers. In Ideotypical CML cells (i.e. those that express the fusion protein), the two different detection domains (2a, 2b) may bind to bring two activation domains (3a,3b) together. These activation domains may interact, causing DISC formation and cell death. This may eliminate cancerous cells.

In treating cancers, IMPs may have the distinct advantage that they may only substantially affect targeted ideotypical cancer cells. This may spare non-malignant cells from the effects of treatment. Current cancer treatments often employ drugs that disrupt cell growth, but this disruption causes severe collateral damage and side-effects. By sparing non-malignant cells, IMPs may avert the substantial side-effects of chemotherapeutics and radiation therapies. Further, chemotherapeutics and radiation therapies take a shotgun approach to proliferating cells. Newer therapies and the human immune system do attempt to create a more targeted response by recognizing such cells externally, but cancerous cells mutate rapidly and their surface antigens are often hidden. IMPs, on the other hand, may target all rather than just a subset of cancerous cells by recognizing epitopes inside the cell that are less likely to be hidden or mutable. This improved combination of specificity and efficacy of treatment may result in complete eradication of cancers in some patients.

While the above example describes IMPs using embodiments against particular cancer-associated antigens, many different embodiments are possible for various cancers and patient types. Further, aberrant nucleotide strands or other metabolites may provide similarly efficacious epitopes to be detected. These examples above should not be construed as limiting other embodiments that target cancers.

D. Embodiments as May be Used in Treating Extracellular Bacterial Infections

Various embodiments of IMPS may also be used to treat extracellular infections. As with antivirals, existing treatments for bacterial diseases (i.e. antibiotics) favor natural selection of pathogens that evolve resistance mechanisms. Antibiotic resistance is a common problem, especially in environments like hospitals where antibiotics and multiple disease-causing organisms are frequently brought into contact. A related problem with antibiotics is their non-specificity against virulent bacteria. The term "virulent" as used herein refers to the state of any resident organism in which the organism expresses genes that help it to cause disease in a host organism. Most bacteria found in and on human beings are not virulent and are sometimes called "avirulent" strains. Unfortunately, antibiotics commonly target both virulent and avirulent organisms. Further, many virulent strains—including XDR Tuberculosis and MRSA—are those which have developed the strongest resistance mechanisms to existing antibiotics. Thus treating an individual with antibiotics may actually help the virulent strains to spread by removing avirulent strains that are competing for the same resources.

To further complicate matters, any given bacterium can switch from being avirulent to being virulent by expressing virulence genes. The terms "virulence genes" and "virulence factors" as used herein refer to the genes and gene products of a resident organism that help it to cause disease in a host organism. Virulence factors may include various toxins, adhesion molecules (invasins), secretion system proteins, enzymes, capsule proteins, and immunosuppressants, to name a few. Not all strains of bacteria in a given species express or even possess virulence genes at any given time. However, all organisms that are virulent at any given time express some virulence genes. The expression of mRNA and protein from these virulence genes in high levels may be unique to virulent cells, making them ideotypical. Note that these ideotypical cells are not human, but rather are bacterial cells.

In a particular embodiment of IMPs (1a,2b) targeting virulent Staphylococcus aureus, detection domains (2a,2b) could comprise an antibody fragment that is specific for alpha-hemolysin or Hla (4). Hla is an especially potent toxin expressed only in virulent Staph aureus and not in avirulent strains of the same bacterium. An activation domain (3) could comprise a monomer of an antibacterial toxin that is effective only as a dimer. If adjacent epitopes on alpha-hemolysin are detected by the detection domains (2a,2b) inside Staph cells of the virulent ideotype, the activation domains (3a,3b) may be brought into contact and dimerize. This may cause the death of virulent bacteria but spare avirulent strains and species.

The embodiment above and other embodiments of IMPS may have a number of advantages over existing antibiotics. First, IMPs may circumvent the resistance mechanisms of currently-resistant bacteria. Second, in potentially-virulent strains IMPs may help naturally select variant strains that do not express virulence factors. This means that the evolutionary pressure exerted by IMPS may exactly oppose that of classical antibiotics. Classical antibiotics select for strains that can express virulence genes that directly inactivate the antibiotics, whereas IMPS may select for strains that avoid expressing virulence factors altogether. Third, IMPs may not affect avirulent commensal organisms. This means that patients using IMPS may not be susceptible to other infections as they would be when taking antibiotics. IMPS may actually give avirulent commensal organisms an evolutionary advantage over virulent organisms, keeping the patient's balance of bacterial flora in a favorable equilibrium.

E. Embodiments as May be Used in Eradicating Vector-borne Parasites

Various embodiments of IMPS could also be used to treat vector-borne parasites. The term "vector-born parasites" as used herein refers to parasitic organisms that are transferred to humans and/or to other animals by a "vector" organism like a mosquito, a tick, or some other intermediary. These parasites can include bacteria, fungi, yeasts, and protozoa. These diseases present a particular problem in that there are often vast reservoirs of infection. The term "reservoir" as used herein refers to animals other than humans in which a parasitic organism can grow and multiply and eventually be transferred by a vector to other animals or to humans. A reservoir may or may not experience a disease state from the parasite. Examples of such parasites and their diseases include sleeping sickness and Chagas disease (caused by trypanosomes from tsetse flies and assassin bugs, respectively), Lyme disease (caused by *Borrelia burgdorferi* from ticks), and Tularemia (caused by *Francisella tularensis* from various arthropods), to name a few.

Vector abatement programs have been used against such parasites, notably the malaria-causing protozoan parasite *Plasmodium falciparum*. The mosquitoes that carry malaria have been the target of such programs in which chemicals are used to deplete the population of potential carriers. Unfortunately, this has not eradicated the disease. First, killing all mosquitoes of a given species would be very difficult. Second, even killing the vast majority of mosquitoes of a given species would have unexpected and potentially-hazardous environmental consequences because of the ecological niche that the mosquitoes fill. The killing of reservoir animals from which vectors pick up the disease could have similarly dire consequences.

In one particular embodiment of IMPs, malaria-carrying mosquitoes may be targeted. Note here that an entire organism—a mosquito—can be grouped into two designated ideotypes: carrier and non-carrier. A detection domain (2) may comprise an antibody fragment specific for var gene products that are expressed copiously on the surface of the protozoa. An activation domain (3a,3b) may comprise an inactive subunit of an arthropod-specific toxin. In this embodiment, heterodimerization or heteromultimerization may produce an active toxin. Such an embodiment may be introduced to mosquitoes by injecting it into a species that the vector mosquitoes generally feed on. As the mosquito ingests the blood of the animal, it also ingests the IMPs (1). It may also be introduced by providing it in available water sources. In mosquitoes that are not colonized by *Plasmodium* (i.e. non-carrier ideotype), the IMPs (1) have no epitopes (4) to bind and may therefore be inert. In carrier mosquitoes, however, the activation domains (3a,3b) may dimerize or multimerize to form the full toxin. In the presence of sufficient toxin, the carrier mosquito may die.

A similar embodiment to target malaria-carrying mosquitoes may have the same detection domain (2) but have activation domains (3a,3b) on different IMPS comprised of either a pro-toxin or a weakened enzyme to convert the toxin into its active form. As the detection domains (2) of two different IMPS (1a,1b) bind to adjacent epitopes (4), the pro-toxin (3a) and weak enzyme (3b) interact as may not be possible in solution because of the enzyme's relative non-specificity. Once the pro-toxin is converted in sufficient amounts, the carrier may die.

The embodiment above and other embodiments of IMPS against carriers of vector-borne parasites may have a number of advantages. IMPs may target only those vectors that are actually of the carrier ideotype. Since this may be just a fraction of the vector population, it may allow the ecological niche that would be vacated by expired carriers to be filled seamlessly by non-carriers of the same species. This may minimize the environmental impact of the treatment. Further, IMPS in this example may promote the natural selection of vectors of any given species that are themselves resistant to colonization by the parasite. In some diseases, species that are resistant to colonization have already been described. These populations may be enriched in areas where carriers are selected against because of the added evolutionary advantage. The end goal of these treatments may be to eliminate transmission to human hosts. By cutting off the vector source of the parasite, the parasite may no longer be transmitted. Without such transmission, the disease may be eradicated entirely from a single region or from the world at large. Additionally, all this may be accomplished without immunization of the human population.

The above example is illustrative of the use of IMPS against vector-borne malaria. However, many other embodiments of IMPs targeting various parasitic diseases in various ways are possible. Further, other embodiments may be used to target malaria. For example, an embodiment may be introduced to the potential-carrier vector population by various other means including by directly feeding the vector a solution containing IMPS. These feedings may be protected such that a feeding station may not itself become colonized by the parasite. Thus the above examples should not be considered limiting.

F. Embodiments as May be Used in Autoimmune Disorders

Various embodiments of IMPS could also be used to treat a variety of autoimmune disorders. The terms "autoimmune disorder," "autoimmune disease," or "autoimmune syndrome" as used herein refer to any disease in which the human immune system causes or exacerbates the disease. This may include classical autoimmune disorders like Systemic Lupus Erythematosus (SLE), Rheumatoid Arthritis (RA), and Type I Diabetes as well as immunoproliferative disorders (cancers involving immune cells), transplant scenarios, allergies, and infectious diseases in which primary harm is caused by the immune system.

B and T cells of the immune system are both major and unique cells in the human body. They express a wide variety of receptors called antigen receptors, which bind various antigens throughout the body. The term "antigen receptor" as used herein refers to receptors on the B cell that are also often referred to as the B cell receptor (BCR), membrane-bound Ig (mIg), and antibodies (Ab) as well as to receptors on the T cell that are also referred to as the T cell receptor (TCR). Each clonal population of B or T cells only expresses one antigen receptor that is specific to a particular antigen. The term "clonal" as used herein refers to a group of cells that come from the same parent B or T cell. Clonal cells may be cells of a single ideotype, meaning cells that express similar epitopes (e.g. the antigen receptor).

Figure 5:
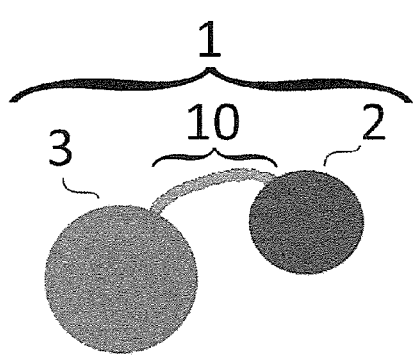
FIG. 5 shows a detection domain linked to an activation domain by a linker according to one embodiment.

FIG. 5 shows a detection domain (2) linked to an activation domain (3) by a linker (10) according to one embodiment. A detection domain (2) may be an antigen for which a clonal (and ideotypical) subpopulation of cells expresses a particular antigen receptor. An activation domain (3) may be FasL. FasL is a molecule that, when trimerized, may interact with the receptor Fas on the surface of nucleated cells to induce downstream signals that cause the death of the cell.

Figure 6:
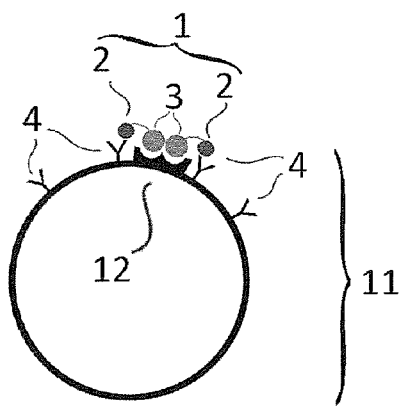
FIG. 6 shows the binding of a plurality of Ideotypically Modulated Pharmacoeffectors to the surface antigen receptors of ideotypical disease-causing B cells according to one embodiment.

FIG. 6 shows the binding of a plurality of Ideotypically Modulated Pharmacoeffectors (1) to the surface antigen receptors (4) of ideotypical disease-causing B cells (11) according to one embodiment. As in FIG. 5, a detection domain (2) may be an antigen for which a clonal, ideotypical subpopulation of cells expresses a particular antigen receptor and an activation domain (3) may be FasL. The detection domains (2) may bind the antigen receptors (4) of the disease-causing cells (11). When a plurality of Ideotypically Modulated Pharmacoeffectors binds, the FasL activation domains (3) trimerize. When FasL has trimerized, it may interact with the receptor Fas (12) on the surface of the cells to induce downstream signals. These downstream signals may cause the death of the cell.

In a particular IMP embodiment to treat an immunoproliferative disorder like Burkitt's lymphoma, the malignant B or T cell population is derived from a single cell. This means that the malignant cell population is clonal and each of these cells expresses the same or closely-related antigen receptor (i.e. has the same ideotype). The embodiment's detection domain (2) may be an antigen for which the antigen receptors (4) of cancerous cells are specific. In the case of an immunoproliferative disorder, an ELISA screen of potential antigens may elucidate which antigen this should be. The embodiment's activation domain (3) may be FasL, which is a ligand that—when trimerized—may interact with the Fas receptor found on all nucleated cells' surfaces. The targeted antigen receptors (4) may interact with IMPs on ideotypical disease-causing cells through the detection domain (2). This may bring a plurality of activation domains (3) into close proximity and they may trimerize. As a result of this trimerization, these activation domains may interact with the Fas receptor (12) on the surface of said cells to cause downstream signaling that induces apoptosis in the cell. The death of these cells may clear the disease.

Note: The previous embodiment and several embodiments that follow may cause some confusion. If the embodiment is against a B cell malignancy, an antibody (antigen receptor) on the surface of said B cells may actually provide the epitopes (4) to which the detection domains (2) bind. On the other hand, in other embodiments previously listed an antibody may be part of the embodiment's detection domain. In this example, however, the detection domain (2) may comprise the antigen for which said antigen receptors (4) are specific. In an embodiment against a B cell malignancy, the detection domain (2) may also comprise an antibody that is specific for the membrane-bound antibody.

Other IMP embodiments may be used to treat patients with classical autoimmune disorders like Systemic Lupus Erythematosus (SLE). Classically-defined autoimmune diseases generally follow a pattern of mistakes in the screening of B and T cells that are reactive to self antigens. The term "self antigen" as used herein refers to proteins and other metabolites produced by the human body. When B and T cells are reactive to self antigens, such cells are termed "autoreactive." When these cells escape the screening processes of the body, they can cause damage and interrupt important processes in the body. In patients with SLE, for instance, disease-related B and T cells are autoreactive to nuclear antigens. The detection domain (2) of an embodiment may comprise such nuclear antigens. These could be determined by ELISA. The activation domain (3) of an embodiment may comprise FasL as in some previous embodiments. Once introduced into the blood stream or lymph, a plurality of IMPs (1) would bind the antigen receptors (4) of the autoreactive cell ideotype (11). This would bring the activation domains (3) of multiple IMPs (1) together to trimerize. Trimerized activation domains (3) may interact with the Fas receptor (12) on said cells, inducing apoptosis of the cell. Since the epitope (i.e. antigen receptor specific for the detection domain) may not be present on the surface of cells that do not contribute to disease, these cells may be spared. In some autoimmune disorders, multiple ideotypes may be present and may be targeted with separate embodiments.

Note: T cell antigen receptors (TCRs) differ from B cell receptors (BCRs) in that they recognize an antigen in the context of an MHC molecule on other cells. In targeting autoreactive T cells, therefore, some adjustment in the detection domain may be necessary to accommodate this difference. This may include adding an MHC motif to the detection domain (2).

Other IMP embodiments may be used to combat allergies. The terms "allergy" and "allergies" as used herein refer to immune responses against otherwise-innocuous foreign antigens. The term "foreign antigens" refers to metabolites (e.g. proteins, lipids, carbohydrates) that were not produced by the body. Innocuous foreign antigens are often found in the body and should not normally cause an immune response. B cells producing a certain class of antibody against these antigens are a major part of many of these hypersensitivities. Like the previously-mentioned embodiment, an embodiment for the purpose of clearing B cells of the allergy-causing ideotype may have a detection domain (2) that is the foreign antigen. The activation domain (3), as previously, may be FasL. As before, the detection domains (2) may only bind the antigen receptors (i.e. epitopes) of ideotypical disease-causing cells (11). The activation domains (3) may trimerize and interact with the Fas receptors (12) on the cell surface, causing apoptosis.

Other IMP embodiments may further be used to combat graft-versus-host disease (GVHD). In GVHD, transplanted tissues retain their immunogenicity in the new host and cause damage to the host's existing tissues. This is generally considered the opposite of transplant rejection, wherein the transplant actually rejects the host. Donor tissue's natural killer and NK T cells, which have specific antigen receptors called KIRs for donor cells' unique MHC molecules, fail to recognize the new host tissue and therefore determine that it is foreign. This leads to the "rejection" of the host by the donor tissue, and an immune response is mounted against the host. In one embodiment, the detection domain (2) may be the donor cells' MHC molecules. The activation domain (3) may be FasL. As in the previous examples, Ideotypically Modulated Pharmacoeffectors (1) may bind the antigen receptors of disease-causing (NK and NK T) cells (11). The activation domains (3) may in turn trimerize and signal death through the Fas receptor (12). This may clear the donor tissue of unwanted immune cells and may avert GVHD.

On the other hand, other IMP embodiments may also be used to combat transplant rejection. Transplant rejection is the rejection of donor tissue by the host, which is handled by at least two ideotypical sets of host cells. One subset is host T cells with antigen receptors (TCRs) that recognize the unique MHC of the donor tissue. Another subset is host B cells that produce anti-donor-MHC antibodies. These antibodies are a common cause of long waits on donor waiting lists for patients receiving transplants after a previous rejection. When the MHC of the donor tissue does not match the MHC of the host, these cells induce death in donor cells. An IMP embodiment to combat transplant rejection may have a detection domain (2) that is a mimetic of the donor's MHC molecules. An activation domain (3) may be FasL. The detection domain (2) may bind the antigen receptors (4), whether TCRs or BCRs, of host T and B cells. The activation domains (3) may trimerize and interact with Fas receptors (12) on the offending T and B cells (11). This may signal cell apoptosis. If these subsets of host cells are ablated, a graft rejection may be avoided.

It should be noted that, in any of the above embodiments or other embodiments dealing with antigen receptors, soluble B cell receptors (i.e. secreted antibodies) may need to be cleared prior to treatment by plasmapheresis or some other method in order to give an embodiment clear access to the membrane-bound receptors.

The previous examples of embodiments for various autoimmune disorders should not be construed as limiting. Different detection domain (2) and activation domain (3) combinations may be used and different embodiments and applications are possible. Each of these example embodiments and other embodiments not listed here may offer a number of advantages, mostly having to do with treatment specificity and efficacy. In the case of immunoproliferative disorders, IMP embodiments may clear the malignancy and restore the patient to normal status without the side-effects of chemotherapeutic and radiation therapy methods. In the case of autoimmune disorders, embodiments may clear the offending autoreactive B and/or T cells at the center of the disorder, either ameliorating symptoms or curing the disease. In the case of the twin diseases of GVHD and transplant rejection, these combined embodiments may increase the likelihood of transplant success. All this may be accomplished without the immunosuppression that is a common feature of most treatments for this group of diseases. This may be especially important because many of these patients are already immunocompromised.

G. Embodiments as May be Used in Ameliorating Cellular Disease and/or Enhancing Cellular Function In some cellular diseases, certain subsets of cells fail. These cells may have a given task, like providing structural strength to surrounding tissue or providing an important hormone or metabolite to other parts of the body. A number of embodiments may induce the production of metabolites in such cells to improve their function. For instance, muscular atrophy occurs in a number of diseases. One embodiment may have a detection domain (2) for troponin (4), a metabolite produced in large quantities in muscle cells. An activation domain (3) may be subunits of an enzyme to help assemble actin subunits, adding strength to said muscle when the activation domains are brought together.

Some embodiments may be effective in patients with Type II Diabetes. In this form of diabetes, pancreatic beta cells producing insulin are overwhelmed with the production demands incurred by high sugar and lipid levels in the blood. An IMP may help by encouraging these ideotypical pancreatic beta cells or their stem cell progenitors to proliferate, or perhaps by increasing the anti-apoptotic pathways in existing beta cells. These IMPS may extend the life of these cells and may avert or postpone the onset of serious complications of disease.

Adipose cells may also offer a good target for some embodiments to combat lipodystrophic disease. In such diseases, adipose cells are unable to handle the volume of fats in the bloodstream. This leads to disease. By interacting with such cells specifically, their capacity may be adjusted or their survival pathways may be bolstered. Activation domains (3) of some IMP embodiments may interact with cellular pathways to decrease the efficiency of energy expenditure in the cell, depleting excessive energy stores.

Some current treatments for cellular diseases have non-optimal success rates as a result of collateral cell damage, especially amongst a certain subset of cells. Some embodiments may help ameliorate these side-effects in conjunction with other treatments by bolstering particular cell subsets (i.e. neurons, muscle cells, etc) from the effects of treatment. The previous examples of embodiments for various cellular applications should not be construed as limiting. Each of these example embodiments and other embodiments not listed here may offer a number of advantages, mostly having to do with treatment specificity and efficacy.

H. Embodiments as May be Used in Research Applications

Various embodiments of IMPS could be used in research applications. For instance, one embodiment may have a detection domain that is specific for proteins involved in cell differentiation. An activation domain (3) may be an inactive monomer of a fluorescence protein. The embodiment may be introduced to a cell tissue culture. When the protein (4) is present in any given cell, the detection domain (2) may bind it. Adjacent activation domains may dimerize to form an active fluorescent dimer, allowing visualization of the location and concentration of proteins in the cell as well as visualization of the cells expressing the protein.

Another embodiment may have a detection domain for mRNAs encoding certain proteins. A detection domain (2) may be an antisense nucleotide strand against the mRNAs (4). An activation domain (3) may be inactive subunits of an enzyme that cleaves mRNAs. In this case, when the mRNAs are produced in the cell, the detection domains may bind to adjacent RNA sequences. This may bring the subunits together, which may go on to cleave mRNA and limit its expression in the cell.

The above examples are illustrative of just a few of the ways in which IMPs could be used in a laboratory setting. Many other embodiments may exist for various other potential applications in research.

I. Summary of Example Embodiments

Although the above descriptions include a number of specific applications, these should not be considered limiting. Various techniques may be used in different contexts, and various contexts may benefit from different techniques and embodiments. For example, while a pouch-based embodiment in FIG. 4 has been mentioned in an example of an embodiment that may help treat a Chlamydia infection, a pouch-based embodiment may also be employed against ideotypical carrier vectors of a disease like malaria. Similarly, while an embodiment with a nucleotide sequence for a detection domain (2) has been mentioned in an example of an embodiment that may help treat an HIV infection, an embodiment with a nucleotide sequence detection domain (2) may be used in treating a cancer with characteristic mRNA (4) in the cytosol. Thus a number of variations may be applied without departing from the scope of the present disclosure. In addition, not all applications are part of the embodiments presented here. Thus the scope of the invention should be evaluated according to the appended claims.

The invention claimed is:

1. A method comprising:
introducing a plurality of engineered Ideotypically Modulated Pharmacoeffectors (IMPs) into a population of cells, each IMP comprising:
a detection domain that has affinity for an epitope, wherein the detection domain binds single-stranded nucleotide sequences, and
an activation domain coupled to the detection domain;
binding the detection domain of each IMP of a subset of the plurality of IMPs to one or more epitopes; and
in response to binding the detection domain, activating the activation domain of each IMP of the subset of the plurality of IMPs, the activating causing a downstream effect in each cell of at least a subset of the population of cells.

2. The method of claim 1, wherein the downstream effect comprises termination of each cell of the subset of the plurality of cells.

3. The method of claim 1, wherein the population of cells comprises a blood stream.

4. The method of claim 1, wherein the population of cells comprises a tissue culture.

5. The method of claim 1, wherein the population of cells comprises a vector organism.

6. The method of claim 1, wherein binding the detection domain of each IMP of a subset of the plurality of IMPs to one or more epitopes comprises detecting within a cell the one or more epitopes, the detecting using the detection domain of at least one IMP of the subset of the plurality of IMPs.

7. The method of claim 1, wherein binding the detection domain of each IMP of a subset of the plurality of IMPs to one or more epitopes comprises detecting on the surface of a cell the one or more epitopes, the detecting using the detection domain of at least one IMP of the subset of the plurality of IMPs.

8. The method of claim 1, further comprising conjugating the detection domain with the activation domain using a linker molecule.

9. The method of claim 1, wherein the activating of the activation domain comprises binding a subset of the plurality of IMPs to adjacent epitopes, the binding of the subset of the plurality of IMPs causing the activation domains of the subset of the plurality of IMPs to interact with each other.

10. The method of claim 1, wherein the detection domain of each IMP comprises a nucleotide sequence.

11. The method of claim 1, wherein the activation domain of each IMP comprises inactive Caspase-9 monomer.

12. The method of claim 1, wherein the activation domain of each IMP comprises a subunit of a bioactive molecule.

13. The method of claim 1, wherein:
the detection domains comprises one or more nucleotide sequences with affinity for adjacent nucleotide sequences; and
the activation domains comprises monomers of a subunit of a bioactive molecule,
wherein binding the detection domain of each IMP of a subset of the plurality of IMPs to one or more adjacent nucleotide sequences further comprises:
a multimerization or interaction of the monomers of a subunit of a bioactive molecule, and an activation of an activity of one or more said bioactive molecules.

14. The method of claim 1, wherein:
the epitope comprises a single-stranded RNA or DNA nucleotide sequence.

* * * * *